United States Patent [19]

Dreikorn

[11] 3,987,196

[45] Oct. 19, 1976

[54] TETRAZOLO(1,5-a)QUINOXALINES FOR CONTROL OF PHYTOPATHOGENS

[75] Inventor: Barry A. Dreikorn, Indianapolis, Ind.

[73] Assignee: Eli Lilly and Company, Indianapolis, Ind.

[22] Filed: June 10, 1975

[21] Appl. No.: 585,551

[52] U.S. Cl. .............................................. 424/250
[51] Int. Cl.² ...................... A01N 9/00; A01N 9/22
[58] Field of Search .................................... 424/250

[56] References Cited
UNITED STATES PATENTS 3,764,681   10/1973   Dreikorn........................ 260/256.4
3,839,569   10/1974   Dreikorn et al. ................... 424/258

OTHER PUBLICATIONS

Shiho et al., "J. Am. Chem. Soc.", 82, pp. 4044–4054, (1960).

*Primary Examiner*—V. D. Turner
*Attorney, Agent, or Firm*—Joseph A. Jones; Everet F. Smith

[57] ABSTRACT

The protection of plants from foliar and soil-borne phytopathogens is accomplished by the treatment of the plants with a specified class of tetrazolo[1,5-a]quinoxalines.

11 Claims, No Drawings

TETRAZOLO(1,5-a)QUINOXALINES FOR CONTROL OF PHYTOPATHOGENS

BACKGROUND OF THE INVENTION

This invention belongs to the field of agricultural chemistry, and provides to the art a new method of protecting plants from, and reducing the adverse effects of, foliar and soil-borne phytopathogens. The importance of protecting plants from phytopathogens can hardly be exaggerated. Virtually every ornamental and crop plant suffers from the ravages of phytopathogen-caused plant diseases. Many economically important crops cannot be successfully raised without a chemical agent for the protection of the plant from phytopathogens. Some of the earliest achievements of agricultural chemistry were in the field of plant protection, and the search for new and improved plant protective agents continues to be pursued vigorously.

A few prior publications are important to the understanding of the background of this invention. U.S. Pat. Nos. 3,764,681 and 3,839,569, of the present inventor, disclosed the fungicidal efficacy of tetrazolo[1,5-a]quinolines and s-triazolo[4,3-a]quinolines, respectively. Belgian Pat. No. 803,098 and West German Offenlegungsschrift No. 2,249,350 disclosed that certain imidazoquinoxalines are also useful as agricultural fungicides.

SUMMARY OF THE INVENTION

A new method of reducing the adverse effects of phytopathogens has been discovered. The method comprises contacting the phytopathogens with an effective phytopathogen-inhibiting amount of a compound of the formula

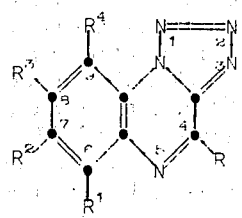

wherein
R represents
 hydrogen,
 $C_1-C_3$ alkyl,
 trifluoromethyl,
 chloro,
 fluoro,
 bromo,
 carbamoyl,
 $C_1-C_2$ alkoxycarbonyl,
 amino,
 $C_1-C_2$ alkylamino,
 di($C_1-C_2$ alkyl)amino,
 hydrazino,
 $C_1-C_2$ alkylhydrazino,
 di($C_1-C_2$ alkyl)hydrazino,
 $C_1-C_2$ alkylcarbonylamino,
 $C_1-C_2$ alkoxycarbonylamino, or
 $-CX_nH_{3-n}$, wherein X represents chloro, fluoro or bromo, and $n$ represents 1-2;

one of $R^1$ and $R^4$ represents hydrogen, and the other represents hydrogen, $C_1-C_3$ alkyl, nitro, chloro or fluoro;

$R^2$ and $R^3$ independently represent hydrogen, $C_1-C_3$ alkyl, trifluoromethyl, chloro or fluoro;

provided that $R^1$, $R^2$, $R^3$ and $R^4$ represent hydrogen when R represents carbamoyl, $C_1-C_2$ alkoxycarbonyl, $C_1-C_2$ alkylcarbonylamino, or $C_1-C_2$ alkoxycarbonylamino;

and further provided that at least three of R, $R^1$, $R^2$, $R^3$ and $R^4$ represent hydrogen, except that R, $R^2$ and $R^3$ may all represent chloro or may all represent methyl; and the 5-oxides of the compounds of the above formula wherein R and $R^1$ represent hydrogen.

DESCRIPTION OF THE PREFERRED EMBODIMENT

The chemical terms used in the above generic formula are used in their normal meanings in organic chemistry. For example, the term $C_1-C_3$ alkyl refers to such groups as methyl, ethyl and isopropyl.

The term $C_1-C_2$ alkoxycarbonyl refers to groups such as methoxycarbonyl and ethoxycarbonyl. The terms $C_1-C_2$ alkylamino and di($C_1-C_2$ alkyl)amino refer to groups such as methylamino, ethylamino and diethylamino.

The terms $C_1-C_2$ alkylhydrazino and di($C_1-C_2$ alkyl)hydrazino refer to such groups as 1-ethylhydrazino, 2-methylhydrazino and 1,2-dimethylhydrazino.

The terms $C_1-C_2$ alkylcarbonylamino and $C_1-C_2$ alkoxycarbonylamino refer to such groups as ethylcarbonylamino, methylcarbonylamino and ethoxycarbonylamino.

It will be understood that the tetrazole moiety of the compounds could be at times in the tautomeric azide form. Spectral evidence indicates that the compounds are primarily in the tetrazole form and remain so under the conditions at which the compounds have usually been handled. However, some conditions of solvent, temperature and pressure could shift the equilibrium to the azide form. Chemists will recognize that the compounds are the same entities, whether they are in the tetrazole or azide form.

All of the compounds named herein are named as tetrazolo[1,5-a]quinoxalines in the interest of uniformity, even though the rules of nomenclature may call for some compounds to be named otherwise.

The compounds below are typical of the compounds used in the invention. It will be understood that the named compounds do not bound the scope of the invention, but are named merely to help those of chemical skill to understand the invention.

4-ethyl-7-methyltetrazolo[1,5-a]quinoxaline
 4-chloromethyl-7-trifluoromethyltetrazolo[1,5-a]quinoxaline
 4-ethylamino-6-methyltetrazolo[1,5-a]quinoxaline
 6-nitro-4-trifluoromethyltetrazolo[1,5-a]quinoxaline
 8-isopropyltetrazolo[1,5-a]quinoxaline, 5-oxide
 9-propyltetrazolo[1,5-a]quinoxaline
 4-(1-methylhydrazino)-8-trifluoromethyltetrazolo[1,5-a]quinoxaline
 7-chloro-4-propyltetrazolo[1,5-a]quinoxaline
 4-dichloromethyl-6-ethyltetrazolo[1,5-a]quinoxaline
 8-ethyl-4-fluorotetrazolo[1,5-a]quinoxaline
 7,8-difluorotetrazolo[1,5-a]quinoxaline
 9-chloro-4-methylaminotetrazolo[1,5-a]quinoxaline
 6-chloro-4-(2-ethylhydrazino)tetrazolo[1,5-a]quinoxaline 8-fluoro-4-isopropyltetrazolo[1,5-a]quinoxaline
8-propyltetrazolo[1,5-a]quinoxaline, 5-oxide
9-nitro-7-trifluoromethyltetrazolo[1,5-a]quinoxaline
4-bromo-9-isopropyltetrazolo[1,5-a]quinoxaline
4-methoxycarbonyltetrazolo[1,5-a]quinoxaline
7-ethyl-4-fluoromethyltetrazolo[1,5-a]quinoxaline
4-(1,2-dimethylhydrazino)tetrazolo[1,5-a]quinoxaline
4-dimethylamino-8-methyltetrazolo[1,5-a]quinoxaline
6-fluorotetrazolo[1,5-a]quinoxaline, 5-oxide
6-nitro-8-trifluoromethyltetrazolo[1,5-a]quinoxaline
4-difluoromethyl-6-propyltetrazolo[1,5-a]quinoxaline, 5-oxide
9-fluorotetrazolo[1,5-a]quinoxaline
4-ethylcarbonylaminotetrazolo[1,5-a]quinoxaline
6-isopropyltetrazolo[1,5-a]quinoxaline, 5-oxide
8-chloro-7-propyltetrazolo[1,5-a]quinoxaline
7-chloro-9-methyltetrazolo[1,5-a]quinoxaline, 5-oxide
7,8-diethyltetrazolo[1,5-a]quinoxaline, 5-oxide
4-methoxycarbonylaminotetrazolo[1,5-a]quinoxaline
8-chloro-9-ethyltetrazolo[1,5-a]quinoxaline, 5-oxide
7-ethyl-6-nitrotetrazolo[1,5-a]quinoxaline
7-chloro-8-trifluoromethyltetrazolo[1,5-a]quinoxaline
8-chloro-7-methyltetrazolo[1,5-a]quinoxaline
6-ethyl-8-fluorotetrazolo[1,5-a]quinoxaline
9-ethyl-7-fluorotetrazolo[1,5-a]quinoxaline, 5-oxide The preferred compounds of this invention, with which the method of the invention is most desirably carried out, are 4-methyltetrazolo[1,5-quinoxaline, 4-chlorotetrazolo[1,5-a]quinoxaline, 4-chloro-6-methyltetrazolo[1,5-a]quinoxaline, 4,7,8-trichlorotetrazolo[1,5-a]quinoxaline, 4-bromomethyltetrazolo[1,5-a]quinoxaline, 6-methyltetrazolo[1,5-a]quinoxaline and tetrazolo[1,5-a]quinoxaline.

The compounds used in this invention are readily obtained by known methods. Some general teaching of the synthesis of the compounds, as well as specific preparative examples, will be given to assure that organic chemists can obtain the compounds. The reader is also referred to Shiho et al., "Studies on Compounds Related to Pyrazine," J. Am. Chem. Soc. 82, 4044–54 (1960), for general discussion of the synthesis.

The starting compounds for the compounds of this invention are appropriately substituted 2-chloroquinoxalines, which are obtainable by well-known processes, such as those discussed by Platt, "2-Hydroxy- and 2-Amino-Derivatives of 6- and 7-Methylquinoxaline," J. Chem. Soc., 1310–13 (1948).

In general, the tetrazolo[1,5-a]quinoxalines are formed by the reaction of the 2-chloroquinoxalines with azide ion in acidic aqueous ethanol. See U.S. Pat. No. 3,764,681 on the preparation of related tetrazoloquinolines. From 1 to 8 hours of reaction time at the reflux temperature is usually adequate to form the product in high yield. When the desired product has a 4-halogen substituent, however, it is best to convert the starting compound to the corresponding 2-hydrazinoquinoxaline and react the intermediate with nitrous acid in acetic acid at low temperature.

The starting compounds are most conveniently made by the reaction of an appropriately substituted o-phenylenediamine with glyoxylic acid in ethanol to form a 2-quinoxalinone. (Platt, supra, shows the compounds as a quinoxalinol.) If the starting phenylenediamine is asymmetrically substituted, as would be the case if, for example, a product having a 7- or 6-substituent were to be made, a mixture of isomeric quinoxalinones will be made. The isomers may be separated at that point, or may be carried through the process as a mixture, and the products separated at any convenient point in the process, or may be used as a mixture. Whether the isomers are separated or not, the quinoxalinone is reacted with a chlorinating agent such as $POCl_3$ to form the corresponding 2-chloroquinoxaline intermediate.

The problem of mixtures of isomeric intermediate compounds can be avoided by an unambiguous method of synthesizing the intermediates. For example, a route can be used which reacts an appropriately substituted o-nitroaniline with cyanoacetic acid to form the correspondingly ring-substituted α-cyano-o-nitroacetanilide. That compound is reacted with base in pyridine to form the 3,4-dihydro-3-oxo-2-quinoxalinecarbonitrile, 1-oxide, which is reduced to the desired 2-quinoxalinone with sodium dithionite. See Ahmad et al., "Quinoxaline Derivatives III", Tetra. 20, 1107–12 (1964), and "Quinoxaline Derivatives IV", Tetra. 21, 861–65 (1965).

In general, the 4-substituent of the products is derived from a corresponding substituent on the glyoxylic acid from which the intermediate is made. In some instances, the 4-substituent of the products must be formed after the tetrazole ring has been closed. For example, mono- and dihalomethyl 4-substituents are made by the halogenation of a 4-methyl substituent as the last stage in the synthesis. A carbamoyl substituent is formed by the amination of a 4-ethoxycarbonyl substituent. An alkylcarbonylamino or alkoxycarbonylamino substituent is formed by the acylation of the corresponding 4-amino substituent.

The 5-oxides are prepared by making an intermediate 3-chloroquinoxaline, 1-oxide, and proceeding with the synthesis as described above. The intermediate is oxidized by the usual reagents such as peracetic acid and peroxybenzoic acids. Cf. Cheeseman, "Recent Advances in Quinoxaline Chemistry", Advances in Heterocyclic Chemistry, Vol. II, 215–16, Academic Press (1963).

Example 1 below shows the general method of synthesis of the products.

EXAMPLE 1

6-methyltetrazolo[1,5-a]quinoxaline

A solution was made of 0.5 g. of 2-chloro-5-methylquinoxaline, 10 ml. of 0.1N HCl and 0.6 g. of sodium azide in 35 ml. of denatured ethanol. The reaction mixture was stirred for 6 hours at reflux temperature. When the mixture was allowed to cool, the product, 6-methyltetrazolo[1,5-a]quinoxaline, crystallized in 91 percent yield and was separated by filtration. The product had a melting point of 160°–62° C., and was identified by nuclear magnetic resonance analysis and elemental microanalysis, the results of which were as follows.

|   | Theoretical | Found |
|---|---|---|
| C | 58.37% | 58.39% |
| H | 3.81 | 3.66 |
| N | 37.82 | 37.75 |

The next example illustrates the synthesis of a 5-oxide of this invention.

EXAMPLE 2 tetrazolo[1,5-a]quinoxaline, 5-oxide

A mixture of 10 g. of 2-chloroquinoxaline and 15 g. of m-chloroperoxybenzoic acid in 250 ml. of chloroform was stirred for 4 hours at room temperature, and then 1 hour at reflux temperature. The residue obtained upon evaporation of the solvent from the reaction mixture was dissolved in ethyl acetate, and the solution was extracted three times with 50 cc. volumes of 5 percent sodium carbonate solution. The organic layer was then washed with water, dried over sodium sulfate, and concentrated to dryness. The residue, after recrystallization, was 6 g. of 3-chloroquinoxaline, 1-oxide, m.p. 148°–50° C.

A 7.5 g. portion of the above intermediate product was dissolved in 200 ml. of ethanol, and 5 g. of sodium azide dissolved in 25 ml. of water was added. The mixture was made acidic with 40 ml. of 2N HCl. The reaction mixture was stirred at reflux temperature overnight. When the mixture was cooled, 6.5 g. of tetrazolo[1,5-a]quinoxaline, 5-oxide, m.p. 192°–94° C., crystallized and was separated by filtration. The elemental analysis was as follows.

|   | Theoretical | Found |
|---|---|---|
| C | 51.34% | 51.49% |
| H | 2.69 | 2.66 |
| N | 37.42 | 37.57 |

The next example shows the unambiguous synthesis of a 9-substituted product.

EXAMPLE 3

9-methyltetrazolo[1,5-a]quinoxaline

A solution was made of 10 g. of 2-methyl-6-nitroaniline and 5.8 g. of cyanoacetic acid in 200 ml. of benzene, and 14 g. of phosphorus pentachloride was added in small portions to the mixture. After the addition was complete, the mixture was stirred at 60° C. for four hours. The reaction mixture was then allowed to cool, and the intermediate product, α-cyano-6'-nitro-o-acetotoluidide, crystallized spontaneously. It was separated by filtration and was washed with benzene. The yield was 13.3 g., and the melting point, after recrystallization from ethanol, was 192°–93.5° C.

Ten g. of the above intermediate product was stirred in a mixture of 50 ml. of pyridine and 50 ml. of 1N NaOH at room temperature for 3 hours. The reaction mixture was then made acidic and 8.5 g. of 3,4-dihydro-5-methyl-3-oxo-2-quinoxalinecarbonitrile, 1-oxide, precipitated from the mixture. The product was recrystallized from ethanol, after which the melting point of the intermediate product was 294° C.

Five g. of the above intermediate product and 10 g. of sodium dithionite were stirred at reflux temperature in 200 ml. of water containing a few milliliters of ethanol. The starting compound soon dissolved, and the solution was then filtered hot, acidified and concentrated under vacuum. The residue was dissolved in 1N NaOH and filtered. The product, 8-methylquinoxaline-2(1H)-one, precipitated from the filtrate upon acidification. The yield was 3.3 g. and the melting point of the product was 267°–70° C.

A 2.2 g. portion of the above intermediate product was stirred with 30 ml. of phosphorus oxychloride as the temperature was brought to reflux and maintained at that temperature for 10 minutes. The cooled solution was concentrated and the resulting oil was dissolved in ethyl acetate. The solution was filtered and washed with 5 percent aqueous sodium carbonate until the washings were alkaline, and then washed with water. The organic phase was dried over sodium sulfate and evaporated to obtain an oil which solidified upon standing.

The crude 3-chloro-5-methylquinoxaline obtained in the step above was stirred for 3 hours at reflux temperature in 75 ml. of ethanol containing 1.8 g. of sodium azide and 20 ml. of 1N HCl. When the reaction mixture was cooled, the product precipitated as needles. Recrystallization of the product from ethanol produced highly purified 9-methyltetrazolo[1,5-a]quinoxaline, m.p. 166°–68° C. The product was identified by NMR analysis and by elemental microanalysis.

|   | Theoretical | Found |
|---|---|---|
| C | 58.37% | 58.11% |
| H | 3.81 | 3.98 |
| N | 37.82 | 37.60 |

The next example illustrates the synthesis of a compound having a 4-halogen substituent.

EXAMPLE 4

4-chlorotetrazolo[1,5-a]quinoxaline

A 3.3 g. portion of anhydrous hydrazine and 10 g. of 2,3-dichloroquinoxaline were refluxed in 200 ml. of methanol for about 20 minutes. The reaction mixture was then allowed to cool, and the intermediate product, 2-chloro-3-hydrazinoquinoxaline, precipitated and was collected by filtration. After the intermedite was washed with water, the yield was 6.7 g. and the melting point was 180° C. dec.

The above intermediate product was dissolved in 60 ml. of glacial acetic acid, and 2.39 g. of sodium nitrite in 5 ml. of water was added. The product precipitated immediately. The reaction mixture was chilled for 1 hour, and the product was collected by filtration, washed with water and air dried. Recrystallization from anhydrous ethanol gave 4.8 g. of 4-chlorotetrazolo[1,5-a]quinoxaline, m.p. 194°–96° C. Results of the elemental microanalysis were as follows.

|   | Theoretical | Found |
|---|---|---|
| C | 46.73% | 46.81% |
| H | 1.96 | 2.13 |
| Cl | 17.24 | 17.07 |
| N | 34.06 | 34.08 |

Example 5 below shows the halogenation of a 4-methyl substituent to form a bromomethyl compound.

EXAMPLE 5

4-bromomethyltetrazolo[1,5-a]quinoxaline

4-dibromomethyltetrazolo[1,5-a]quinoxaline

A mixture of 5 g. of 4-methyltetrazolo[1,5-a]quinoxaline, 5 g. of N-bromosuccinimide, and 0.5 g. of benzoyl peroxide in 1 l. of carbon tetrachloride was irradiated with a sunlamp for 4 hours. The reaction mixture was filtered and concentrated to dryness under vacuum, and the solids were dissolved in benzene and chromatographed on a silica gel column to separate the mono- and dibromemthyl compounds. Benzene was used as the elution solvent. The second fraction off the column contained 4-dibromomethyltetrazolo[1,5-a]-quinoxaline and the third fraction contained 4-bromomethyltetrazolo[1,5-a]quinoxaline. The fractions were individually evaporated to dryness under vacuum, and the products were recrystallized, the dibromo compound from ethanol, and the bromomethyl compound from benzene-cyclohexanone.

The yield of 4-dibromomethyltetrazolo[1,5-a]quinoxaline, m.p. 195°–96° C., was 1.2 g., and the yield of 4-bromomethyltetrazolo[1,5-a]quinoxaline, m.p. 136.5°–37.5° C., was 1.8 g. The compounds were identified by NMR analysis and by elemental microanalysis, the results of which follow.

EXAMPLE 5A 4-dibromomethyltetrazolo[1,5-a]quinoxaline

|   | Theoretical | Found |
|---|---|---|
| C | 31.52% | 31.80% |
| H | 1.47 | 1.45 |
| N | 20.42 | 20.70 |
| Br | 46.59 | 46.36 |

EXAMPLE 5B 4-bromomethyltetrazolo[1,5-a]quinoxaline

|   | Theoretical | Found |
|---|---|---|
| C | 40.93% | 40.72% |
| H | 2.29 | 2.25 |
| N | 26.52 | 26.38 |
| Br | 30.26 | 30.47 |

Synthetic methods typified by the above examples, and explained by the above general description, are used to produce all of the compounds used in this invention. For example, the following typical compounds are produced thereby.

EXAMPLE 6

4-acetamidotetrazolo[1,5-a]quinoxaline, m.p. 243° C. dec.

EXAMPLE 7 mixture of 7-methyltetrazolo[1,5-a]quinoxaline and 8-methyltetrzolo[1,5-a]quinoxaline, m.p. 144°–47° C.

EXAMPLE 8 mixture of 7-chlorotetrazolo[1,5-a]quinoxaline and 8-chlorotetrazolo[1,5-a]quinoxaline, m.p. 185°–91° C.

EXAMPLE 9 mixture of 7-chloro-4-methyltetrazolo[1,5-a]quinoxaline and 8-chloro-4-methyltetrazolo[1,5-a]quinoxaline, m.p. 133°–35° C.

EXAMPLE 10 mixture of 7-chloro-9-nitrotetrazolo[1,5-a]quinoxaline and 8-chloro-6-nitrotetrazolo[1,5-a]quinoxaline, m.p. 138°–39° C.

EXAMPLE 11

4-methyltetrazolo[1,5-a]quinoxaline, m.p. 154°–55.5° C.

EXAMPLE 12

4-diethylaminotetrazolo[1,5-a]quinoxaline, m.p. 120°–21° C.

EXAMPLE 13 tetrazolo[1,5-a]quinoxaline, m.p. 199° C. dec.

EXAMPLE 14

4-aminotetrazolo[1,5-a]quinoxaline, m.p. 273°–74° C. dec.

EXAMPLE 15

7,8-dimethyltetrazolo[1,5-a]quinoxaline, m.p. 199°–201° C.

EXAMPLE 16

4-ethoxycarbonylaminotetrazolo[1,5-a]quinoxaline, m.p. 185°–87° C.

EXAMPLE 17

4-ethoxycarbonyltetrazolo[1,5-a]quinoxaline, m.p. 167°–69° C.

EXAMPLE 18

4-carbamoyltetrazolo[1,5-a]quinoxaline, m.p. 216° C. dec.

EXAMPLE 19 mixture of 7-trifluoromethyltetrazolo[1,5-a]quinoxaline and 8-trifluoromethyltetrazolo[1,5-a]quinoxaline, m.p. 99°–101° C.

EXAMPLE 20 mixture of 4,7-dimethyltetrazolo[1,5-a]quinoxaline and 4,8-dimethyltetrazolo[1,5-a]quinoxaline, m.p. 103°–05° C.

EXAMPLE 21

7,8-dichlorotetrazolo[1,5-a]quinoxaline, m.p. 208° C. dec.

EXAMPLE 22

4,7,8-trimethyltetrazolo[1,5-a]quinoxaline, m.p. 190°–92° C.

EXAMPLE 23

4-chloro-6-methyltetrazolo[1,5-a]quinoxaline, m.p. 197°–98° C.

EXAMPLE 24

4,7,8-trichlorotetrazolo[1,5-a]quinoxaline, m.p. 211°–14° C.

EXAMPLE 25

4-hydrazinotetrazolo[1,5-a]quinoxaline, m.p. 208° C. dec.

EXAMPLE 26

4-methyl-8-trifluoromethyltetrazolo[1,5-a]quinoxaline, m.p. 127°–29° C.

EXAMPLE 27

4,6-dimethyltetrazolo[1,5-a]quinoxaline, m.p. 174°–76° C.

EXAMPLE 28 mixture of 6,8-dichlorotetrazolo[1,5-a]quinoxaline and 7,9-dichlorotetrazolo[1,5-a]quinoxaline, m.p. 118°–21° C.

EXAMPLE 29 mixture of 6-nitrotetrazolo[1,5-a]quinoxaline and 9-nitrotetrazolo[1,5-a]quinoxaline, m.p. 117°–18° C.

EXAMPLE 30

7-fluorotetrazolo[1,5-quinoxaline, m.p. 169°–70° C.

The compounds described above have been shown in a number of in vivo tests to protect plants from the adverse effects of phytopathogens. The following examples illustrate the tests employed and the results produced by representative compounds.

In most of the tests, each compound was formulated for testing by dissolving or suspending about 3.5 weight percent of it in 50:50 acetone:ethanol containing about 10 g./100 ml. of a nonionic surfactant. The solution was then dispersed in deionized water in a quantity such that the water dispersion contained the various compound concentrations indicated in the specific test methods and the tables below. Concentrations are measured in parts per million by weight.

The compound dispersions were applied to the test plants, in tests against foliar phytopathogens, by spraying them with an air atomizer, using sufficient dispersion to wet the plants thoroughly. Other methods of compound formulation and application were used in some tests as described in the specific test methods below.

Untreated, infected controls and untreated, normal controls were included in each test. The results are reported on a 1–5 rating scale were 1 indicates severe disease and 5 indicates complete control of the disease. An empty space in the tables below shows that the indicated compound was not tested at the indicated rate. In some cases, more than one test was performed against a given phytopathogen, and the results in such cases are reported as averages. Compounds are identified by the example numbers used above.

The following test methods were used.

TEST 1 helminthosporium leaf spot of wheat

Healthy wheat seed was planted in sterile greenhouse soil. When the seedlings were 4–5 inches tall, they were sprayed with test compound dispersions at compound concentrations indicated in the table below. The day after treatment, the plants were inoculated with a spore suspension of *Helminthosporium sativum* which had been grown on potato dextrose agar. The plants were placed in a moist growth chamber for two days to start disease growth, and were then transferred to the greenhouse. About a week after treatment, the plants were observed and the results were recorded.

TEST 2 late blight of tomato

Four-week-old tomato seedlings were sprayed with aqueous dispersions containing test compounds at compound concentrations indicated in the table below. The following day, the foliage was inoculated with an aqueous suspension of propagules of *Phytophthora infestans*. The inoculum had been reared on infected wheat seed. The plants were held for two days in a moist chamber, and were then transferred to the greenhouse. The plants were observed and rated for disease control about one week after application of the test compounds.

TEST 3 powdery mildew of bean

The host plants were 10-day-old bean seedlings. After aqueous dispersions containing test compounds at compound concentrations indicated in the table below had been sprayed on the foliage of the beans and allowed to dry, the plants were placed in the greenhouse and inoculated by storing them under other bean plants which were heavily infected with powdery mildew (*Erysiphe polygoni*). After about 10 days, the plants were observed and the results recorded as usual.

TEST 4 anthracnose of cucumber

Aqueous dispersions containing test compounds at compound concentrations indicated in the tables below were applied to healthy cucumber seedlings grown in sterilized greenhouse soil. The following day, the plants were inoulated with *Collectotrichum lagenarium* conidia as an aqueous suspension. The fungus had been grown on potato dextrose agar in petri dishes. The plants were held in a moist chamber for two days and transferred to the greenhouse, and the disease was observed and rated approximately 12 days after application of the test compounds.

TEST 5 rice blast of rice

The test compound dispersions, at compound concentrations indicated in the tables below, were applied to healthy rice seedlings growing thickly in plastic pots. The plants were inoculated on the next day with *Piricularia oryzae* (grown on rice polish agar) and the plants were held in a moist chamber for two days. The plants were then held in the greenhouse for 5–7 days and observed.

TEST 6 bean rust of bean

Pinto bean seedlings were raised in plastic pots in the greenhouse. One week after the seeds were planted, 10 ml. of an aqueous dispersion of the compound to be tested was added to the soil in which each treated plant was growing. The following day, the plants were inoculated with spores of bean rust (*Uromyces phaseoli* var. typica) which were grown on pinto bean plants and applied to the test plants as an aqueous dispersion. The plants were held for two days in a moist chamber, transferred to the greenhouse, and observed about 10 days after inoculation with the phytopathogen.

TEST 7 bacterial wilt of tomato

Tomato seedlings were grown in the greenhouse in plastic pots. When the plants were about 30 days old, aqueous dispersions of the compounds to be tested were sprayed on the treated plants. On the following day, the plants were inoculated with *Pseudomonas solanacearum* by inserting a toothpick, soaked in a bacterial broth culture, at a leaf stem junction. The plants were then moved to the greenhouse, and kept for two days under a translucent plastic hood. The hood was removed on the third day in the greenhouse, and the plants were observed and the results recorded after about one week in the greenhouse.

TEST 8 bacterial blight of soybean

Soybean seedlings, about 8 days old, growing in plastic pots were sprayed with aqueous dispersions of the test compounds. On the next day, the treated plants were inoculated by spraying the lower leaf surfaces with a water suspension of *Pseudomonas glycinea*. The plants were then handled as in the test immediately above, except that they were observed about 6 days after inoculation.

TEST 9 crown gall of tomato

Tomato seedlings were grown in plastic pots. About 4 weeks after the seeds were planted, each seedling was inoculated with a water suspension of *Agrobacterium tumefaciens* by passing a needle dipped in the suspension through the stem of each plant. The roots of the inoculated plants were then washed free of the sand in which the plants had been grown, and each plant was placed in a large test tube which contained the test chemical at a concentration shown in the tables below. The plants were held in the greenhouse for about 10 days, after which they were observed and the results recorded.

TEST 10 pythium damping-off of cotton

An aqueous dispersion of each compound to be tested was prepared by first dissolving 114 mg. of the compound in 2 ml. of acetone/ethanol, and then dispersing the solution in about 30 ml. of water containing 0.1 percent of a nonionic surfactant.

Soil was infected with *Pythium aphanidermatum*, the causative organism of pythium damping-off disease, by growing four separate isolates of the organism in cornmeal and adding portions of all four cultures to greenhouse soil which had previously been sterilized to kill wild organisms.

Four ml. of the test compound dispersion was added to 150 g. of infected soil by absorbing the dispersion on granular clay particles and mixing the particles through the soil. The treatment rate was equivalent to 44.8 kg./ha. Lower rates were used in some tests, as shown below. The soil was then transferred to a small plastic pot which was planted with 12 cotton seeds. The pots were watered and placed in a moist growth chamber until the cotton seedlings emerged, when the pots were transferred to the greenhouse for observation. Disease ratings were made 14 days after planting the seed.

TEST 11 fusarium root rot of bean

The compounds were tested in a procedure essentially similar to the procedure of Test 10, except that the infecting organism was *Fusarium solani* f. phaseoli, the causative organism of fusarium root rot, which was grown in sand mixed with fusarium-infected wheat seed. The host plant was bean, of which three seeds were planted in each pot.

TEST 12 rhizoctonia damping-off of cotton

The test was conducted, in general, according to the method used in the pythium damping off test. The phytopathogen was *Rhizoctonia solani*, strain 700, which was grown on cornmeal.

TEST 13 verticillium wilt of cotton

The test was conducted according to the general method of the pythium damping off test. The phytopathogen was *Verticillium albo-atrum*, stain V3H.

TEST 14 verticillium wilt of tomato

This test was performed as was the test described above except that the host plant was tomato seedlings.

Table 1

| Compound of Example No. | Appln. Rate ppm. | Late Blight | Powdery Mildew | Bean Rust | Anthracnose | Rice Blast | Helminthosporium | Crown Gall | Bacterial Blight | Bacterial Wilt |
|---|---|---|---|---|---|---|---|---|---|---|
| 1 | 400 | 2 | 1 |  | 3.5 | 3 | 1 |  | 1 | 1 |
|  | 80 |  |  |  | 3 | 2 |  |  |  |  |
|  | 40 |  |  | 1 |  |  |  | 5 |  |  |
|  | 20 |  |  |  |  |  |  | 1 |  |  |
|  | 16 |  |  |  | 1 | 1 |  |  |  |  |
|  | 10 |  |  |  |  |  |  | 1 |  |  |
| 2 | 400 | 1 | 1 |  | 3.5 | 2.5 | 1 |  | 1 | 1 |
|  | 80 |  |  |  | 3 | 3 |  |  |  |  |
|  | 40 |  |  | 1 |  |  |  | 3 |  |  |
|  | 16 |  |  |  | 1 | 1 |  |  |  |  |
| 3 | 400 | 1 | 1.7 |  | 4 | 3.3 | 1 |  |  |  |
|  | 100 |  |  | 2.3 |  |  |  |  |  |  |
|  | 80 |  |  |  | 4.5 | 4.5 |  |  |  |  |
|  | 16 |  |  |  | 4 | 4 |  |  |  |  |
|  | 3.2 |  |  |  | 3.5 | 3 |  |  |  |  |
| 4 | 400 | 4.5 | 1 |  | 4.5 | 4.5 | 3 |  |  | 1 |
|  | 80 | 3 |  |  | 1 | 2 | 3 |  |  |  |
|  | 40 |  |  | 1 |  |  |  | 1 |  |  |
|  | 16 | 1 |  |  | 1 | 1 | 1 |  |  |  |
| 5A | 400 | 3.5 | 1 |  | 3 | 3 | 3 |  | 1 | 1 |
|  | 80 | 3 |  |  |  |  |  |  |  |  |
|  | 40 |  |  | 1 |  |  |  | 5 |  |  |

Table 1-continued

| Compound of Example No. | Appln. Rate ppm. | Late Blight | Powdery Mildew | Bean Rust | Anthracnose | Rice Blast | Helminthosporium | Crown Gall | Bacterial Blight | Bacterial Wilt |
|---|---|---|---|---|---|---|---|---|---|---|
|  | 16 | 1 |  |  |  |  |  |  |  |  |
| 5B | 400 | 1 | 3 |  | 1 | 3 | 2 |  |  |  |
|  | 80 |  | 1 |  |  | 1 |  |  |  |  |
|  | 16 |  | 1 |  |  | 1 |  |  |  |  |
| 6 | 400 |  | 1 |  | 1 | 3 | 1 |  | 1 | 1 |
|  | 40 |  |  | 1 |  |  |  | 1 |  |  |
| 7 | 400 |  | 1 |  | 1 | 4 | 1 | 1 | 1 | 1 |
|  | 80 |  |  |  |  | 2 |  | 1 |  |  |
|  | 40 |  |  | 1 |  |  |  | 4 |  |  |
|  | 16 |  |  |  |  | 1 |  | 1 |  |  |
| 8 | 400 | 1 | 1 |  | 1 | 2 | 1 |  | 1 | 1 |
|  | 40 |  |  | 1 |  |  |  | 1 |  |  |
| 9 | 400 | 1 | 1 |  | 1 | 1 | 1 |  | 1 | 1 |
|  | 40 |  |  | 1 |  |  |  | 4.5 |  |  |
| 10 | 400 | 1 | 1 |  | 1 | 1 | 1 |  | 1 | 1 |
|  | 40 |  |  | 1 |  |  |  | 3 |  |  |
|  | 20 |  |  |  |  |  |  | 1 |  |  |
|  | 10 |  |  |  |  |  |  | 1 |  |  |
| 11 | 400 | 2 | 1 |  | 4 | 4.5 | 1 |  |  | 1 |
|  | 80 |  |  |  | 2 | 2 |  |  |  |  |
|  | 40 |  |  | 3 |  |  |  | 1 |  |  |
|  | 16 |  |  |  | 1 | 1 |  |  |  |  |
| 12 | 400 | 1 | 3.5 |  | 1 | 1 |  |  |  | 1 |
|  | 80 |  | 1 |  |  |  |  |  |  |  |
|  | 40 |  |  | 1 |  |  |  | 1 |  |  |
|  | 16 |  | 1 |  |  |  |  |  |  |  |
| 13 | 400 | 1 | 1 |  | 4.5 | 4 |  |  | 1 | 1 |
|  | 80 |  |  |  | 4.3 | 3.7 |  |  |  |  |
|  | 40 |  |  | 1 |  |  |  | 1 |  |  |
|  | 16 |  |  | 1 | 2.2 | 3 |  |  |  |  |
|  | 3.2 |  |  | 1 | 1 | 3 |  |  |  |  |
| 14 | 400 | 3 | 1 |  | 1 | 1 |  |  | 1 | 1 |
|  | 40 |  |  | 1 |  |  |  | 1 |  |  |
| 15 | 400 | 2 | 1 |  | 3 | 1 | 1 |  |  | 1 |
|  | 40 |  |  | 1 |  |  |  | 1 |  |  |
| 16 | 400 | 3 | 1 |  | 1 | 1 | 1 |  |  | 1 |
|  | 40 |  |  | 1 |  |  |  | 1 |  |  |
| 17 | 400 | 3 | 1 |  | 1 | 3 | 1 |  | 1 |  |
|  | 40 |  |  | 1 |  |  |  | 1 |  |  |
| 18 | 400 | 1 | 1 |  | 1 | 3.5 | 1 |  | 1 | 1 |
|  | 80 |  |  |  |  | 3 |  |  |  |  |
|  | 40 |  |  | 1 |  |  |  | 3 |  |  |
|  | 16 |  |  |  |  | 2 |  |  |  |  |
| 19 | 400 | 1 | 1 |  |  |  |  |  | 1 | 1 |
|  | 40 |  |  | 1 |  |  |  | 4.5 |  |  |
|  | 20 |  |  |  |  |  |  | 1 |  |  |
|  | 10 |  |  |  |  |  |  | 1 |  |  |
| 20 | 400 | 1 | 1 |  | 1 | 3 | 1 |  | 1 | 1 |
|  | 40 |  |  | 3 |  |  |  | 1 |  |  |
| 21 | 400 | 1 | 1 |  | 1.6 | 2.5 | 1 |  |  | 1 |
|  | 80 |  |  |  | 2 | 2.5 |  |  |  |  |
|  | 40 |  |  | 1 |  |  |  | 1 |  |  |
|  | 16 |  |  |  | 1 | 2.5 |  |  |  |  |
|  | 3.2 |  |  |  |  | 3 |  |  |  |  |
| 22 | 400 | 1 | 1 |  | 1 | 1 | 1 |  | 1 | 1 |
|  | 40 |  |  | 1 |  |  |  | 1 |  |  |
| 23 | 400 | 4 | 1 |  | 3 | 3 | 4 |  | 1 | 1 |
|  | 80 | 1 |  |  |  |  | 3 |  |  |  |
|  | 40 |  |  | 1 |  |  |  | 1 |  |  |
|  | 16 | 1 |  |  |  |  | 1 |  |  |  |
|  | 3.2 | 1 |  |  |  |  | 1 |  |  |  |
| 24 | 400 | 3 | 1 |  | 3 | 3 | 3 |  | 1 | 1 |
|  | 80 | 2 |  |  |  | 2 | 3 |  |  |  |
|  | 40 |  |  | 1 |  |  |  | 1 |  |  |
|  | 16 | 1 |  |  |  | 1 | 1 |  |  |  |
| 25 | 400 | 2 | 1 |  | 1 | 3 | 1 |  | 1 | 1 |
|  | 40 |  |  | 1 |  |  |  | 1 |  |  |
| 26 | 400 | 1 | 1 |  | 1 | 1 | 1 |  |  | 1 |
|  | 40 |  |  | 3 |  |  |  | 1 |  |  |
| 27 | 400 | 2 | 1 |  | 3 | 4.2 | 1 |  | 1 | 1 |
|  | 80 |  |  |  |  | 2 |  |  |  |  |
|  | 40 |  |  | 1 |  |  |  | 1 |  |  |
|  | 16 |  |  |  |  | 1 |  |  |  |  |
| 28 | 400 | 2.5 | 1 |  | 3 | 3.6 | 1 |  | 1 | 1 |
|  | 80 | 1 |  |  | 2 | 1.5 |  |  |  |  |
|  | 40 |  |  | 1 |  |  |  | 1 |  |  |
|  | 16 | 2 |  |  | 1.5 | 1 |  |  |  |  |
| 29 | 400 | 1 | 1 |  | 1 | 3 | 1 |  |  |  |
| 30 | 400 | 1 | 1 |  | 4.3 | 2.6 | 1 |  |  |  |
|  | 100 |  |  | 1 |  |  |  |  |  |  |
|  | 80 |  |  |  | 3 | 3.5 |  |  |  |  |
|  | 16 |  |  |  | 1 | 2.5 |  |  |  |  |

Table 2

| Compound of Example No. | Appln. Rate kg./ha. | Fusarium Root Rot (bean) | Pythium Damping-off (cotton) | Rhizoctonia Damping-off (cotton) | Verticillium Wilt (cotton) | Verticillium Wilt (tomato) |
|---|---|---|---|---|---|---|
| 4 | 44.8 | 3.6 | 1 | 2 | 1 | |
|   | 22.4 | 3 | | | | |
|   | 11.2 | 2 | | | | |
| 5A | 44.8 | 1 | 1 | 3 | 1 | |
| 6 | 44.8 | 4 | 1 | 2 | 1 | 1 |
|   | 22.4 | 3 | | | | |
|   | 11.2 | 1 | | | | |
| 7 | 44.8 | 1 | 1 | 1 | 1 | |
| 8 | 44.8 | 4 | 2 | 1 | 1 | |
|   | 22.4 | 1 | | | | |
|   | 11.2 | 1 | | | | |
| 9 | 44.8 | 3 | 1 | 1 | 1 | |
| 10 | 44.8 | 3 | 1 | 1 | 1 | |
| 11 | 44.8 | 1 | 1 | 1 | 1 | |
| 12 | 44.8 | 1 | 1 | 1 | 1 | |
| 14 | 44.8 | 3 | 1 | 1 | | 1 |
| 15 | 44.8 | 1 | 2 | 1 | 1 | |
| 16 | 44.8 | 3 | 3 | 1 | 1 | |
|   | 22.4 | 1 | 3 | | | |
|   | 11.2 | 1 | 1 | | | |
| 18 | 44.8 | 1 | 1 | 1 | 1 | |
| 19 | 44.8 | 1 | 1 | 4 | | |
| 21 | 44.8 | 1 | 1 | 1 | 1 | |
| 22 | 44.8 | 5 | 1 | 1 | 1 | |
|   | 22.4 | 3 | | | | |
|   | 11.2 | 1 | | | | |
| 24 | 44.8 | 1 | 1 | 1 | 1 | |
| 25 | 44.8 | 1 | 1 | 1 | 1 | |

This invention is a method of reducing the adverse effects of phytopathogens which comprises contacting the phytopathogens with an effective phytopathogen-inhibiting amount of one of the compounds described above. The method is carried out by applying a compound described above to the foliage of plants or to the soil in which the plants grow, where the compound contacts the phytopathogens. The preferred use of the method is in reducing the adverse effects of phytopathogens, particularly *Piricularia oryzae*, on the foliage of rice.

Practice of the method does not necessarily kill the contacted phytopathogens. As the data above show, application of a sufficient amount of a compound of the invention to inhibit the phytopathogens reduces the adverse effects of the disease, even if less than all of the pathogens are killed by the compound.

As is usual in the plant protection art, best results are obtained by applying the compound several times during the growing season at intervals of from one to a few weeks, depending on the weather and the severity of the disease.

The methods of formulating the compounds and preparing dispersions of the formulations, and the methods of applying dispersions of the compounds to the plants to be protected, are entirely conventional in the plant protection art. Some explanation of the methods of application will be given merely to assure that those skilled in the art can carry out the invention without undue experimentation.

It is usual in describing foliar applications of plant protectants to measure the application rate by the concentration of the dispersion in which it is applied. The application rate is measured in this way because it is customary to apply a sufficient amount of the dispersion to cover the foliage with a thin film. The amount of dispersion applied is thus dependent on the foliar area of the plants being treated, and the quantity of plant protecting compound is dependent upon its concentration in the dispersion.

Compound concentrations in the range of from about 25 to about 1500 parts of compound per million parts by weight of the dispersion are used in the practice of this invention, when the compound is applied to the foliage. Of course, from time to time, higher or lower concentrations will be useful, depending on the severity of the infection and the characteristics of the specific compound in use. The named range, however, encloses the usual optimum concentrations of the compounds.

When soil applications of plant-protecting compounds are made, it is most meaningful to describe the application rate in terms of the amount of compound applied per unit area of soil. Compound application rates in the range of from about 10 to about 50 kg./ha. are used in the practice of this invention when the method is used to protect plants against soil-borne phytopathogens. As previously described, application rates higher and lower than the named range will at times be useful.

The dispersions in which the compounds are applied to foliage are most often aqueous suspensions or emulsions prepared from concentrated formulations of the compounds. Such water-suspendible or emulsifiable formulations are either solids usually known as wettable powders or liquids usually known as emulsifiable concentrates. Wettable powders comprise an intimate mixture of the active compound, an inert carrier and surfactants. The concentration of the active compound is usually from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants used for wettable powders.

Adjuvants are frequently used to improve the ability of the aqueous dispersion to coat and adhere to foliage. Such adjuvants as gums, emulsified polybutenes, cationic surfactants and lignin derivatives can often increase the potency of the method in a specific use.

Less frequently, the compounds are applied in the form of dusts. Agricultural chemical dusts typically comprise the compound in a finely powdered form, dispersed in a powdered inert carrier. Most often, the carrier is a powdered clay, such as pyrophyllite, bentonite, a volcanic deposit, or montmorillonite. Dusts are usually prepared to contain concentrations of the compound at the highest part of the concentration range, such as 1500 ppm., and may contain even more active ingredient.

Dispersions of the compounds are applied to foliage in the usual manners. Low-pressure sprayers, high-pressure sprayers and low-volume air blast equipment are all effective for the application of water-dispersed compounds of the invention. Dust dispersions are readily applied by means of the usual equipment which blows the dust into intimate contact with the foliage.

The same types of dispersions used for application to plant foliage can also be applied to the soil. In addition, the compounds can economically and conveniently be applied to the soil in the form of granular formulations. Such formulations, well known to the agricultural chemical art, are prepared by dispersing the compound on an inert carrier of controlled granular character. Most often, the carrier is a coarsely ground clay, such as attapulgite or kaolin clay, having a particle size in the range of from 0.5 to 3 mm. Such granular formulations are easily applied to the soil with applicators which are specially designed to apply accurately controlled amounts of the granular products to the soil.

I claim:

1. A method of reducing the adverse effects of fungal phytopathogens which comprises contacting the phytopathogens with an effective phytopathogen-inhibiting amount of a compound of the formula

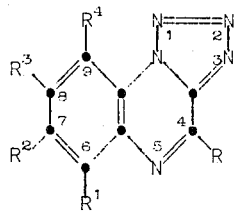

wherein
R represents
 hydrogen,
 $C_1-C_3$ alkyl,
 trifluoromethyl,
 chloro,
 fluoro,
 bromo,
 carbamoyl,
 $C_1-C_2$ alkoxycarbonyl,
 amino,
 $C_1-C_2$ alkylamino,
 di($C_1-C_2$ alkyl)amino,
 hydrazino,
 $C_1-C_2$ alkylhydrazino,
 di($C_1-C_2$ alkyl)hydrazino,
 $C_1-C_2$ alkylcarbonylamino,
 $C_1-C_2$ alkoxycarbonylamino, or
 $-CX_nH_{3-n}$, wherein X represents chloro, fluoro or bromo, and $n$ represents 1-2;
one of $R^1$ and $R^4$ represents hydrogen, and the other represents hydrogen, $C_1-C_3$ alkyl, nitro, chloro or fluoro;
$R^2$ and $R^3$ independently represent hydrogen, $C_1-C_3$ alkyl, trifluoromethyl, chloro or fluoro;
provided that $R^1$, $R^2$, $R^3$ and $R^4$ represent hydrogen when R represents carbamoyl, $C_1-C_2$ alkoxycarbonyl, $C_1-C_2$ alkylcarbonylamino, or $C_1-C_2$ alkoxycarbonylamino;
and further provided that at least three of R, $R^1$, $R^2$, $R^3$ and $R^4$ represent hydrogen, except that R, $R^2$ and $R^3$ may all represent chloro or may all represent methyl; and the 5-oxides of the compounds of the above formula wherein R and $R^1$ represent hydrogen.

2. A method of claim 1 wherein the compound is applied to the foliage of plants, and the concentration of the compound is from about 25 to about 1500 ppm.

3. A method of claim 2 wherein the plants are rice plants.

4. A method of claim 1 wherein the compound is applied to the soil, and the amount of the compound is from about 10 to about 50 kg./ha.

5. A method of claim 1 wherein the compound is 4-methyltetrazolo[1,5-a]quinoxaline.

6. A method of claim 1 wherein the compound is 4-chlorotetrazolo[1,5-a]quinoxaline.

7. A method of claim 1 wherein the compound is 4-chloro-6-methyltetrazolo[1,5-a]quinoxaline.

8. A method of claim 1 wherein the compound is 4,7,8-trichlorotetrazolo[1,5-a]quinoxaline.

9. A method of claim 1 wherein the compound is 4-bromomethyltetrazolo[1,5-a]quinoxaline.

10. A method of claim 1 wherein the compound is 6-methyltetrazolo[1,5-a]quinoxaline.

11. A method of claim 1 wherein the compound is tetrazolo[1,5-a]quinoxaline.

* * * * *